United States Patent
Bae et al.

(10) Patent No.: US 9,566,304 B2
(45) Date of Patent: Feb. 14, 2017

(54) PHARMACEUTICAL COMPOSITION FOR PREVENTING OR TREATING CANCERS COMPRISING DENDRITIC CELLS WITH DAB2 GENE SILENCED

(71) Applicant: Research & Business Foundation Sungkyunkwan University, Suwon-si (KR)

(72) Inventors: Yong-Soo Bae, Suwon-si (KR); Se Eun Byeon, Suwon-si (KR); Selim Ahmed, Suwon-si (KR); Yideul Jeong, Yongin-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/535,876

(22) Filed: Nov. 7, 2014

(65) Prior Publication Data
US 2015/0283176 A1    Oct. 8, 2015

(30) Foreign Application Priority Data
Apr. 8, 2014    (KR) ........................ 10-2014-0041687

(51) Int. Cl.
| | | |
|---|---|---|
| *C12N 15/11* | (2006.01) | |
| *C12Q 1/68* | (2006.01) | |
| *C07H 21/04* | (2006.01) | |
| *A61K 35/15* | (2015.01) | |
| *C12N 5/0784* | (2010.01) | |
| *A61K 39/00* | (2006.01) | |

(52) U.S. Cl.
CPC ........... *A61K 35/15* (2013.01); *A61K 39/0011* (2013.01); *C12N 5/0639* (2013.01); *A61K 2039/5154* (2013.01); *C12N 2501/998* (2013.01); *C12N 2510/00* (2013.01)

(58) Field of Classification Search
None
See application file for complete search history.

(56) References Cited

U.S. PATENT DOCUMENTS

2009/0246179 A1* 10/2009 Penn ...................... A61K 35/28
424/93.7

FOREIGN PATENT DOCUMENTS

| KR | 10-1169331 B1 | 7/2012 |
|---|---|---|
| WO | WO 2011/066475 A1 | 6/2011 |

OTHER PUBLICATIONS

Restifo et al., Nature Reviews Immunology 2012, 12(4), 269-281.*
Md. Selim Ahmed, et al. "Dab2 Induced during DC Development Acts as an Immune Regulator for DC Immunogenicity". The 2013 Fall Conference of the Korean Association of Immunologists, 2013 (3 pages).

* cited by examiner

*Primary Examiner* — Doug Schultz
(74) *Attorney, Agent, or Firm* — NSIP Law

(57) ABSTRACT

Provided is a pharmaceutical composition for preventing or treating cancer, and more particularly, a pharmaceutical composition for preventing or treating cancer, including dendritic cells with a knock-down Dab2 gene. The composition includes a dendritic cell in which a Dab2 gene is knocked down or knocked out or activity of a Dab2 protein is suppressed as an active ingredient, and thus is expected to be useful as a pharmaceutical composition to prevent, improve or treat cancer as a result of having improved antigen uptake, a migration ability of a cell to a lymph node, and expression of inflammatory cytokines, and activating antigen-specific cytotoxic T cell lymphocyte (CTL) and related T cells that can attack cancer cells, and therefore is expected to be used as the pharmaceutical composition for preventing, improving or treating cancer.

8 Claims, 11 Drawing Sheets

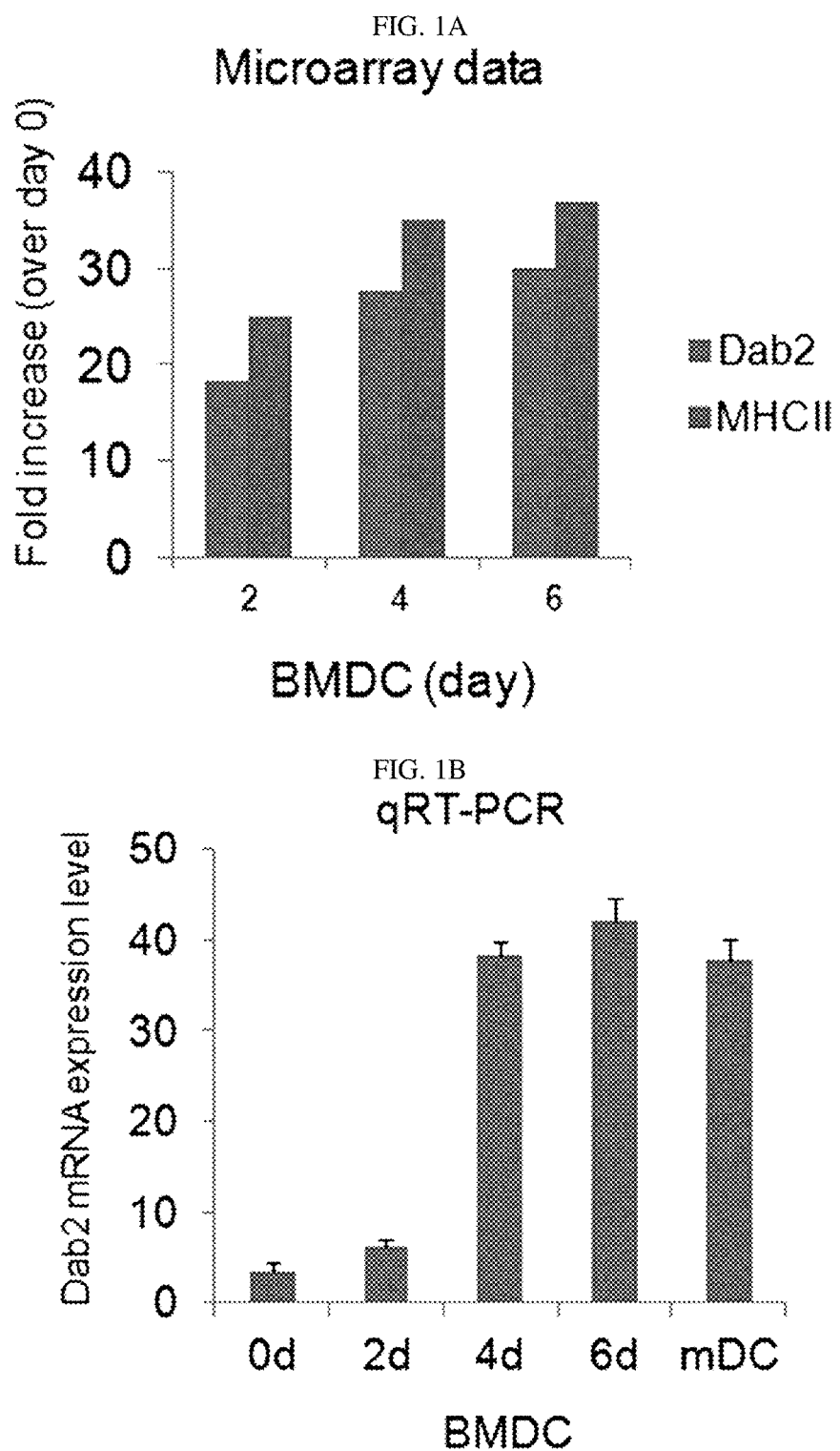

BMDC

Splenic DC

FIG. 3A
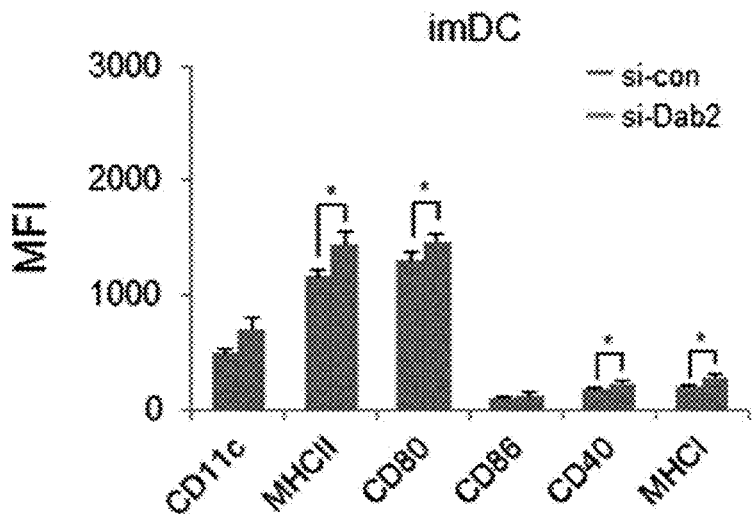
FIG. 3B
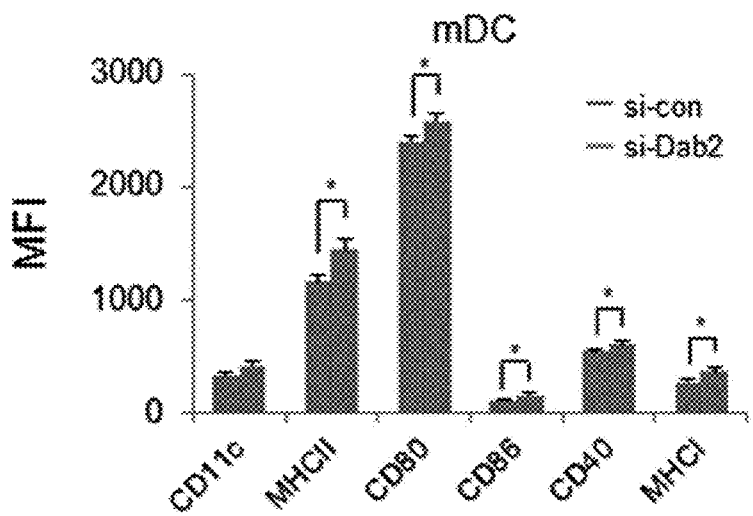

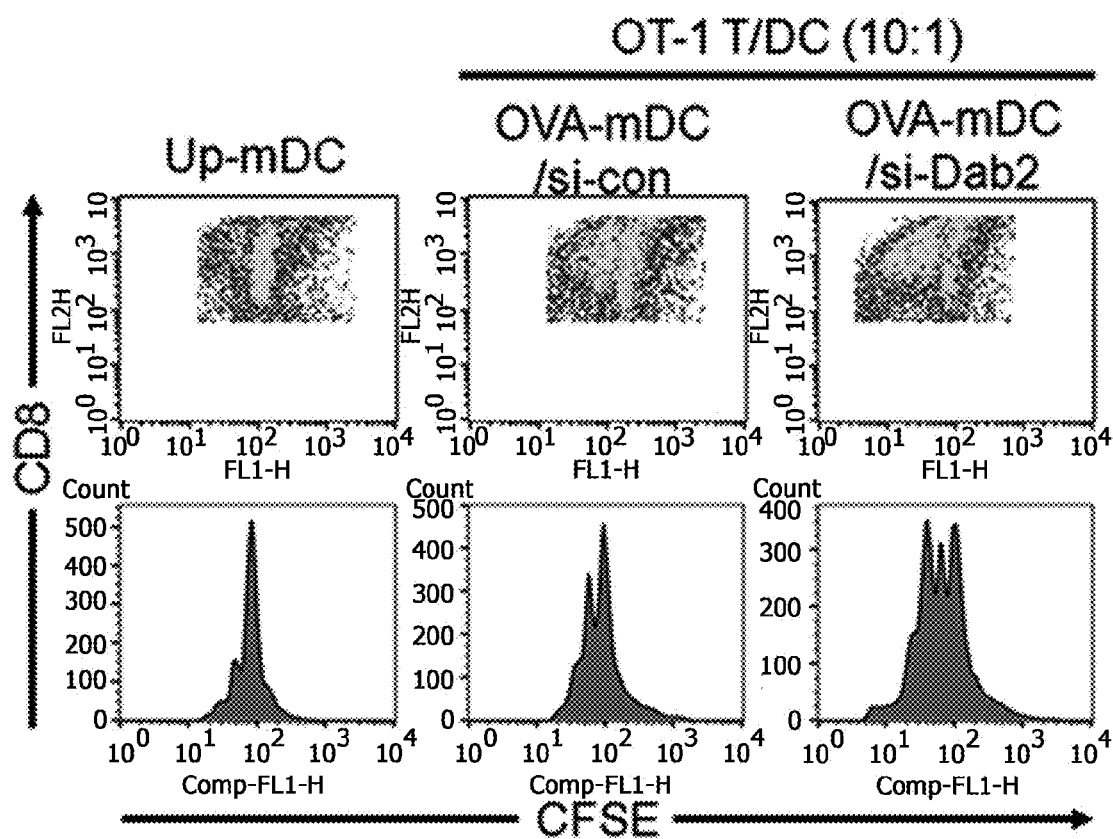

FIG. 7A
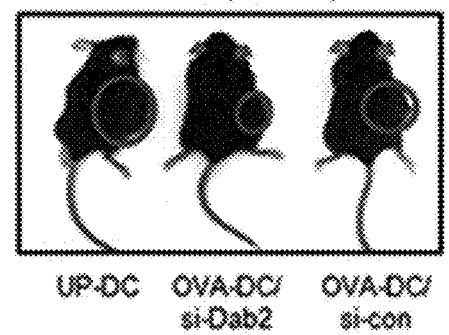
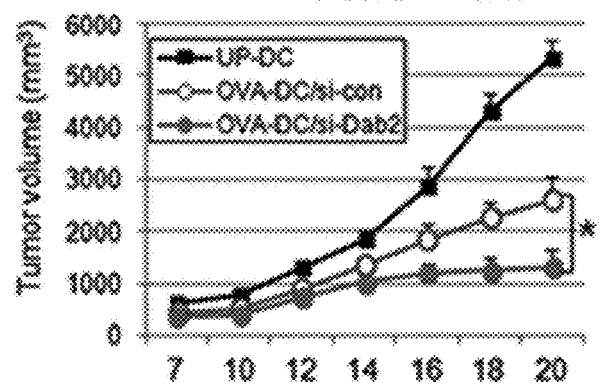
FIG. 7B
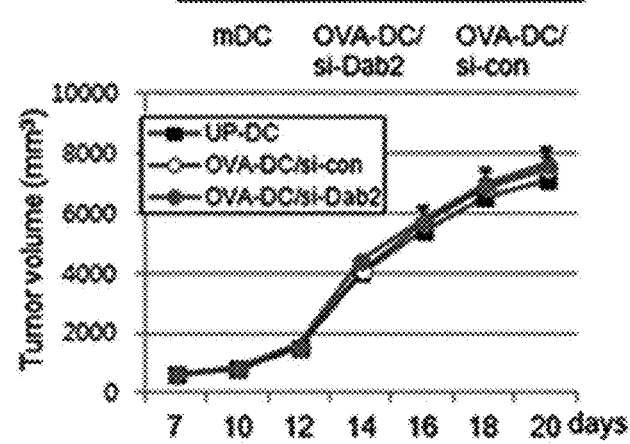

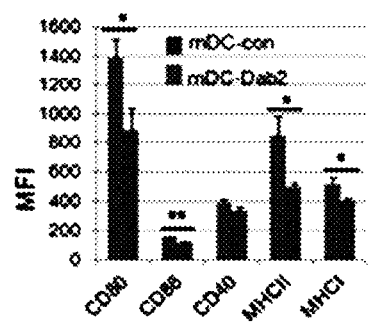
FIG. 8C
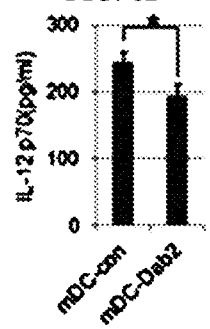
FIG. 8D
FIG. 8E
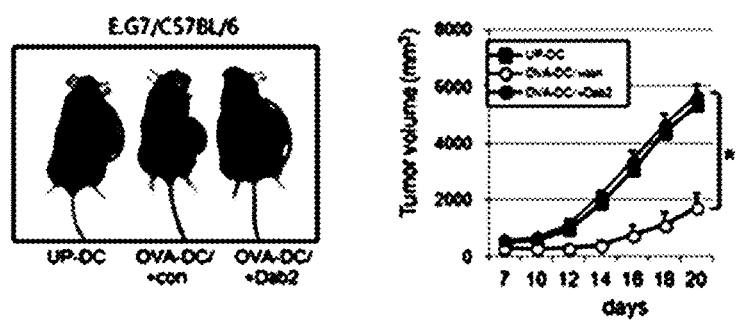

PHARMACEUTICAL COMPOSITION FOR PREVENTING OR TREATING CANCERS COMPRISING DENDRITIC CELLS WITH DAB2 GENE SILENCED

CROSS-REFERENCE TO RELATED APPLICATION

This application claims priority to and the benefit under 35 U.S.C. §119(a) of Korean Patent Application No. 10-2014-0041687, filed on Apr. 8, 2014, in the Korean Intellectual Property Office, the disclosure of which is incorporated herein by reference in its entirety for all purposes.

BACKGROUND

1. Field

The present disclosure relates to a pharmaceutical composition for preventing or treating cancer, and more particularly, to a pharmaceutical composition for preventing or treating cancer that includes dendritic cells with a knockdown disabled 2 (Dab2) gene.

2. Discussion of Related Art

Dendritic cells (DCs) are antigen-presenting cells (APCs) which play a critical role in the initiation of an antigen-specific adaptive immune response. DCs have various characteristics according to their origin, phenotype, function, and maturation process. Generally, to be used in DC studies, DCs are prepared by extracting mouse bone marrow stem cells or human monocytes and differentiating the stem cells or monocytes in media, to which granulocyte-macrophage colony stimulating factor (GM-CSF) and IL-4 are added in vitro. However, an in vivo mechanism for differentiation of bone marrow stem cells into DC, and their maintenance, is little known. Environmental or genetic factors are also critical factors in DC differentiation, but are not known so far. DCs may be critical in stimulating or suppressing a T cell response depending on the situation, thereby regulating in vivo immune homeostasis. Locally, immune tolerance DCs are involved in an immune inhibition or immune tolerance mechanism through activation of regulatory T cells (Treg cells), and thus a cytokine such as interleukin 10 (IL-10) or a transforming growth factor-β (TGF-β) may be expressed, resulting in immune regulation. Treg cells expressing TGF-β and Foxp3 serve to regulate immune responses, and play important roles in maintaining immune homeostasis.

Meanwhile, a Dab2 gene is well known as an adaptor protein involved in a signal transduction mechanism and endocytosis using several receptors. A Dab2 protein has a phosphotyrosine-binding domain binding to membrane proteins such as a low density lipoprotein receptor (LDL receptor) and a TGF-β receptor at the N-terminus. In addition, Dab2 includes a proline-rich domain (PRD) capable of binding to a protein having an SH3 domain such as Grb2 at the C-terminus. The Dab2 gene expresses two types of proteins including P96 and P67. While the main type, the P96 Dab2 protein, is expressed in adults, the P67 protein is generally expressed during embryonic development.

The Dab2 protein is expressed in cells of various tissues or organs including brain, kidney, ovary, and breast. Dab2 shows a lower expression in several tumor tissues than normal tissue, and in normal cells, Dab2 expression strongly suppresses cell proliferation. Thus, the Dab2 protein is known as a critical tumor suppressor. A mitogen-activated protein kinase (MAPK) signal transduction (Ras-Raf pathway) mechanism is critically useful in cell growth, proliferation, and differentiation. Dab2 competitively binds to Grb2 regulating a growth factor and a Ras pathway with Sos. The tumor suppression mechanism of Dab2 is known to suppress formation of cancer by Wnt in the manner of interrupting an endocytosis mechanism of low-density lipoprotein receptor-related protein 6 (LRP6) through Wnt/β-catenin signal transduction, in which Wnt binds to LRP6 phosphorylated at a S1579 site by a casein kinase 2 (CK2). However, such a tumor suppression mechanism of Dab2 cannot explain regulation of the Wnt/β-catenin signal transduction mechanism essentially involved in thymus differentiation or T cell differentiation, survival, and maturation.

Meanwhile, most known cancer treatments mainly include surgery, anticancer agents, and radiotherapy. However, these treatments are accompanied by, for example, side effects, difficulty in attaining a full recovery, and therefore may not be an optimal fundamental treating method of cancer. Particularly, in the case of metastatic cancer or recurrent cancer, in most cases, it is impossible to apply a surgical treatment. And there is a resistance to a chemotherapeutic agent in many cases. Therefore development of a new treating agent for these cancer patients is eagerly sought. Meanwhile, a recently developed cancer treating agent using DCs (refer to Korean Patent No. 10-1169331), compared to conventional agents, exhibits long-term efficacy due to immunological memory, is very effective and safe in prevention of metastasis or reoccurrence of the same cancer, and thus is expected to be a new anticancer immunotherapy. However, for the last decade, efficacy of a DC vaccine for treating cancer did not show an expected effect, and thus the disclosure of the present application is directed to an increase in efficacy of a DC vaccine.

SUMMARY

This Summary is provided to introduce a selection of concepts in a simplified form that are further described below in the Detailed Description. This Summary is not intended to identify key features or essential features of the claimed subject matter.

In one general aspect, a pharmaceutical composition for preventing or treating cancer includes dendritic cells in which expression of a Dab2 gene or activity of a Dab2 protein is suppressed.

The composition may be wherein the expression of a Dab2 gene was suppressed by knock-down or knock-out of the Dab2 gene.

The composition may be wherein the knock-down was performed by an antisense nucleotide, siRNA, shRNA or a ribozyme, which complementarily binds to mRNA of the Dab2 gene.

The composition may be wherein the knock-out was performed by removing or damaging DNA encoding the Dab2 gene.

The composition may be wherein the activity of the Dab2 protein is suppressed by a compound, a peptide, peptide mimetics, a substrate analog, an aptamer or an antibody, which complementarily binds to the Dab2 protein.

The composition may be wherein the siRNA is represented by a base sequence of SEQ. ID. NO: 7 or SEQ. ID. NO: 8.

The composition may be wherein, in the dendritic cells in which the expression of a Dab2 gene is suppressed, expression of MHCII, CD80, CD86 and CD40 is increased.

The composition may be wherein the composition increases T cell proliferation.

The composition may be wherein the composition increases antigen-specific cytotoxic T cell lymphocytes (CTLs).

The composition may be wherein the cancer is selected from the group consisting of bladder cancer, bone cancer, blood cancer, breast cancer, melanoma, thyroid carcinoma, parathyroid carcinoma, osteomyelitis, rectal cancer, laryngopharyngeal cancer, laryngeal cancer, lung cancer, esophageal cancer, pancreatic cancer, colorectal cancer, gastric cancer, tongue cancer, skin cancer, brain tumor, uterine cancer, head cancer or cervical cancer, gallbladder carcinoma, oral cancer, colon cancer, near-anal cancer, central nerve system (CNS) lymphoma and liver cancer.

In another general aspect, a method of preventing or treating cancers in a subject in need thereof includes administering an effective amount of the above composition to the subject.

The method may be wherein the expression of a Dab2 gene was suppressed by knock-down or knock-out of the Dab2 gene.

The method may be wherein the knock-down was performed by an antisense nucleotide, siRNA, shRNA or a ribozyme, which complementarily binds to mRNA of the Dab2 gene.

The method may be wherein the knock-out was performed by removing or damaging DNA encoding the Dab2 gene.

The method may be wherein the activity of the Dab2 protein is suppressed by a compound, a peptide, peptide mimetics, a substrate analog, an aptamer or an antibody, which complementarily binds to the Dab2 protein.

The method may be wherein the siRNA is represented by a base sequence of SEQ. ID. NO: 7 or SEQ. ID. NO: 8.

The method may be wherein, in the dendritic cells in which the expression of a Dab2 gene is suppressed, expression of MHCII, CD80, CD86 and CD40 is increased.

The method may be wherein the composition increases T cell proliferation.

The method may be wherein the composition increases antigen-specific cytotoxic T cell lymphocytes (CTLs).

The method may be wherein the cancer is selected from the group consisting of bladder cancer, bone cancer, blood cancer, breast cancer, melanoma, thyroid carcinoma, parathyroid carcinoma, osteomyelitis, rectal cancer, laryngopharyngeal cancer, laryngeal cancer, lung cancer, esophageal cancer, pancreatic cancer, colorectal cancer, gastric cancer, tongue cancer, skin cancer, brain tumor, uterine cancer, head cancer or cervical cancer, gallbladder carcinoma, oral cancer, colon cancer, near-anal cancer, central nerve system (CNS) lymphoma and liver cancer.

BRIEF DESCRIPTION OF THE DRAWINGS

FIGS. 1A and 1B show results of (FIG. 1A) a micro array and (FIG. 1B) a qRT-PCR technique to analyze expression of a Dab2 gene in differentiation of bone marrow stem cells into DCs;

FIGS. 3A and 3B show (FIG. 3A) results of a western blot analysis to assess expression of a Dab2 gene in Dab2 knock-down DCs, and (FIG. 3B) phenotypes of DCs identified by knock-down of Dab2;

FIGS. 6A to 6G show (FIG. 6A) results of confirming whether an increase or decrease in cytokines of DC is due to knock-down of Dab2, (FIG. 6B) images of formation of T cell proliferated colonies by the Dab2 knock-down DCs, (FIG. 6C) results of an MTI analysis for T cell proliferation due to Dab2 knock-down DCs, (FIG. 6D) results of an FACS analysis for a proliferation capability of a T cell of Dab2 knock-down DCs after labeled with CFSE, (FIG. 6E) results of confirming an increase or decrease in cytokines secreted from T cells during co-culture of Dab2 knock-down DCs and T cells, (FIG. 6F) results of investigating expression of γ-interferon in culture solutions containing a spleen and a lymph node of an OT-1 mouse vaccinated with Dab2 knock-down DCs, and (FIG. 6G) results of identifying CTL of a spleen and a lymph node of an OT-1 mouse vaccinated with Dab2 knock-down DCs;

FIGS. 7A and 7B show results of confirming an anticancer effect of Dab2 knock-down DCs in (FIG. 7A) an E.G7 tumorous mouse model and (FIG. 7B) an EL4 tumorous mouse model; and FIG. 8A to 8E show (FIG. 8A) results of a western blot analysis to assess Dab2 over-expression in DCs, (FIG. 8B) and (FIG. 8C) results of identifying phenotypes of Dab2-over-expressed DCs, (FIG. 8D) results of confirming an increase or decrease in cytokines secretion in Dab2-over-expressed DCs, and (FIG. 8E) an anticancer effect of Dab2-over-expressed DCs in an E.G7 tumorous mouse model.

DETAILED DESCRIPTION

Figure 2A:
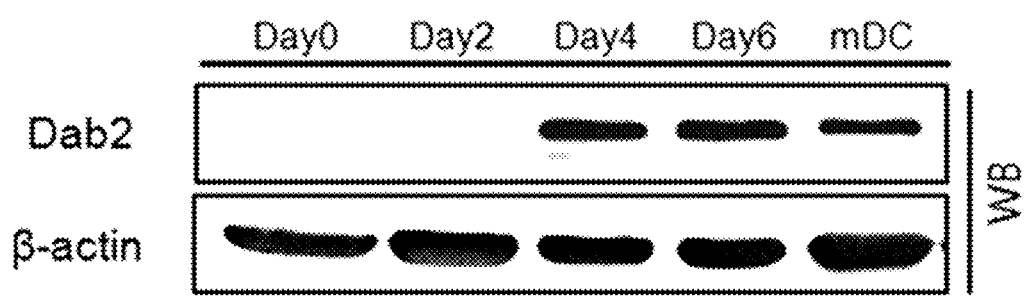
FIGS. 2A and 2B show results of western blot (WB) analysis to assess expression of a Dab2 gene (FIG. 2A) in differentiation of bone marrow stem cells into DC and (FIG. 2B) in DCs isolated from a spleen.

The following detailed description is provided to assist the reader in gaining a comprehensive understanding of the methods, techniques, and/or compositions described herein. However, various changes, modifications, and equivalents of the methods, techniques, and/or compositions described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the disclosure.

It was found that Dab2, which is well known as a tumor suppressor, is highly expressed during DC differentiation. It was surmised that such Dab2 expression affects an activity of inducing anticancer immunity, and therefore, an investigation was conducted with respect to an in vitro immunity-induction capability and an anticancer effect of DCs in a tumorous mouse through a test for knock-down or over-expression of the Dab2 gene. As a result, it was determined that, in Dab2 knock-down DCs, immune-inducing cell surface antigens, C—C chemokine receptor type 7 (CCR7) expression, a lymph node migration capability, a T cell proliferation capability, a cytotoxic T lymphocyte (CTL) induction capability, and a tumor suppression capability are coherently and considerably improved. In addition, it was confirmed that, when Dab2 is over-expressed, the immunity inducing capability and antitumor effect of a DC vaccine disappear. According to such a result, the inventors found that Dab2 served as a regulator for suppressing the immunity induction capability of DCs, and a more effective DC anticancer vaccine could be developed by suppressing or inhibiting Dab2 gene expression.

The present disclosure relates to a pharmaceutical composition for preventing or treating cancer, which includes, as an active ingredient, DCs in which expression of a Dab2 gene or activity of a Dab2 protein is suppressed.

The term "prevention" used herein means all behaviors suppressing cancer or delaying occurrence of cancer by administering a pharmaceutical composition of the present disclosure.

The term "treatment" used herein means all behaviors improving or beneficially changing symptoms caused by cancer due to the administration of the pharmaceutical composition of the present disclosure.

The term "cancer" which is a disease to be improved, prevented or treated by the composition of the present disclosure, includes all diseases caused by cells with aggressive, invasive and metastatic characteristics, thereby propagating to another site of the body. Throughout the specification, cancer also means the same as a malignant tumor, and includes a solid tumor and a blood-borne tumor, but the present disclosure is not limited thereto. For example, in the present disclosure, cancer may be selected from, but is not limited to, the group consisting of bladder cancer, bone cancer, blood cancer, breast cancer, melanoma, thyroid carcinoma, parathyroid carcinoma, osteomyelitis, rectal cancer, laryngopharyngeal cancer, laryngeal cancer, lung cancer, esophageal cancer, pancreatic cancer, colorectal cancer, gastric cancer, tongue cancer, skin cancer, brain tumor, uterine cancer, head cancer or cervical cancer, gallbladder carcinoma, oral cancer, colon cancer, near-anal cancer, central nerve system (CNS) lymphoma and liver cancer.

In the present disclosure, the expression of a Dab2 gene in DC is suppressed by knock-down or knock-out of the Dab2 gene. More specifically, the knock-down is performed by an antisense nucleotide complementarily binding to mRNA of the Dab2 gene, siRNA, shRNA, or a ribozyme, and the knock-out is performed by removing or damaging DNA encoding the Dab2 gene.

In addition, suppression of activity of a Dab2 protein of the present disclosure may be performed by, but not limited to, any one selected from the group consisting of a compound, a peptide, peptide mimetics, a substrate analog, an aptamer and an antibody complementarily binding to the Dab2 protein, and the activity of the Dab2 protein may be suppressed by all of these drugs.

In the present disclosure, the "peptide mimetics" may inhibit the activity of the Dab2 protein by suppressing a binding domain of the Dab2 protein, and the peptide mimetics may be a peptide or a non-peptide, which may be composed of amino acids through non-peptide binding such as psi binding.

In addition, the "aptamer" of the present disclosure is a single-stranded DNA or RNA molecule, which may be yielded by isolating oligomers binding to specific chemical molecules or biological molecules with high affinity and selectivity by an evolving method using oligonucleotide libraries called systematic evolution of ligands by exponential enrichment (SELEX). The aptamer may specifically bind to a target and regulate activity of the target, and for example, may prevent a function of the target through the binding.

Furthermore, the "antibody" of the present disclosure may effectively suppress the activity of Dab2 by specifically and directly binding to Dab2. The antibody specifically binding to Dab2 may use a polyclonal antibody or a monoclonal antibody. The antibody specifically binding to Dab2 may be manufactured by a method known in the art, and as the antibody, a Dab2 antibody commercially known may be purchased to be used.

In the present disclosure, DCs may be derived from a human or a mouse, and preferably may be isolated from human blood, or differentiated into DCs from monocytes isolated from blood or bone marrow stem cells isolated from mouse bone marrow.

In one exemplary embodiment of the present disclosure, during the differentiation into DCs from a bone marrow or spleen of a mouse (refer to Example 1), a Dab2 gene is knock-down in a DC using siRNA of SEQ. ID. NOs: 7 and 8 (refer to Example 2). As a result of identifying changes in phenotype and function, in Dab2 knock-down DCs, expression of MHCII, CD80, CD86, and CD40, which are important to activate T cells, is increased, phagocytosis of DCs is also reinforced, and cell migration capability is also improved (refer to Example 4).

In addition, in another exemplary embodiment of the present disclosure, as a result of identifying a change in ability of inducing T cell immunity by Dab2 knock-down, in Dab2 knock-down DCs, secretion of IL-12 and IL-6 is increased, secretion of IL-10 is decreased, due to Dab2 knock-down DCs, and proliferation of T cells are largely improved (refer to Example 5).

Moreover, in still another exemplary embodiment of the present disclosure, as a result of detecting an anticancer effect using Dab2 knock-down DCs, in a E.G7 tumorous mouse model expressing chicken-derived albumin (OVA), Dab2 knock-down DCs treated with an OVA peptide (OVA-DC/si-Dab2) more effectively suppresses cancer growth than Dab2 normal DCs (OVA-DC/si-con) (refer to Example 6).

The pharmaceutical composition of the present disclosure may further contain at least one of the known active ingredients having an anticancer effect along with all types of DCs in which knock-down and knock-out of a Dab2 gene has occurred and activity of a Dab2 protein is suppressed.

The composition of the present disclosure may further include a carrier, an excipient, and a diluent, which are suitable for and conventionally used in preparation of a pharmaceutical composition. In addition, according to a conventional method, the composition may be used in a dosage form of an oral preparation such as powder, a granule, a tablet, a capsule, a suspension, an emulsion, syrup, or an aerosol, an external preparation, a suppository and a sterile injection. For a suitable preparation known in the art, one that is disclosed in the literature (e.g., Remington's Pharmaceutical Science, Mack Publishing Company, Easton Pa.) is preferably used.

As the carrier, excipient and diluent that may be included in the composition, lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinyl pyrrolidone, water, methyl benzoate, propylhydroxy benzoate, talc, magnesium stearate, or mineral oil may be used. To prepare the composition, a diluent or excipient such as a filler, a thickening agent, a binder, a wetting agent, a disintegrating agent, or a surfactant is generally used.

The pharmaceutical composition of the present disclosure is administered in a pharmaceutically effective amount. The term "pharmaceutically effective amount" used herein denotes a sufficient amount for treating a disease in a benefit/danger ratio that can be applied to medical treatment, and a level of the effective amount may be determined according to factors including a type of a disease, severity, activity of a drug, sensitivity to a drug, administration time, administration route, discharge rate, duration of treatment, and simultaneously-used drugs, and other factors well known in medical fields. The pharmaceutical composition of the present disclosure may be administered alone or in combination with other therapeutic agents, and may be administered sequentially or simultaneously with the conventional therapeutic agent(s) in a single or multiple dose(s). Considering the above factors, it is important to administer the composition at the minimum amount that can obtain the maximum effect without side effects, and the amount that may be easily determined by those of ordinary skill in the art.

Specifically, an effective amount of the pharmaceutical composition of the present disclosure may be determined by a patient's age, sex, condition, weight, absorption rate of an active ingredient in the body, inactivation rate and excretion rate, the type of a disease, or a co-administered drug. Generally, the composition may be administered once to 20 times or more at intervals of at least 2 weeks to 12 months. At each time, $1 \times 10^6$ to $1 \times 10^8$ cells may be administered once or several times a day depending on a patient and an administration route.

The pharmaceutical composition of the present disclosure may be administered to an individual by various routes. All types of administration may be expected, and the composition may be administered by, for example, subcutaneous, intravenous, intramuscular, endometrial, or cerebrovascular injection. The pharmaceutical composition of the present disclosure may be determined according to various related factors such as a disease to be treated, an administration route, a patient's age, sex, and weight, and severity of a disease, and the type of a drug, which is an active ingredient.

The present disclosure also provides a method of treating cancer, which includes administering the pharmaceutical composition to an individual. The "individual" or "subject" used herein means a subject needing to be treated, and more specifically, human or non-human primates, and mammals including mice, rats, dogs, cats, horses, and cows.

Hereinafter, to help in understanding the present disclosure, exemplary examples will be provided. However, the following examples are merely provided to more easily understand the present disclosure.

EXAMPLES

Example 1

Experiment Preparation 1-1. Isolation of Dendritic Cell (DC)

DCs were differentiated from bone marrow stem cells or directly isolated from a spleen, and then cultured. More specifically, bone marrow-derived DCs (BM-DCs) were obtained by isolating bone marrow cells from the femur and tibia of a 6 to 8 week-old female C57BL/6 mouse, and treated with ACK lysis buffer (Lonza) to remove red blood cells. The resulting cells were washed, and cultured in a culture medium (10% FBS and penicillin/streptomycin-contained RPMI 1640) containing 10 ng/ml mGM-CSF (Creagene Inc.). Two days later, a supernatant of the cultured cells was discarded, and exchanged with 2 ml of a new medium containing mGM-CSF. After 4 days of the culture, 1 ml of a new medium containing mGM-CSF was added. After 6 days of the culture, non-binding cells were recovered, and used as immature DCs (imDCs). Mature DCs (mDCs) were cultured by culturing immature DC (imDC) for 24 hours in the presence of LPS (100-200 ng/ml).

In addition, splenic DCs were isolated from the spleen of the 6 to 8 week-old C57BL/6 mouse using CD11c microbeads according to a method provided by Miltenyi Biotec.

1-2. Experimental Method

A. Microarray Analysis

A cDNA microarray was performed at Macrogene Inc. (www.macrogene.com). More specifically, bone marrow cells obtained from a C57BL/6 mouse were cultured for 2, 4, and 6 days under the condition of mGM-CSF, and as a 0-day sample, bone marrow cells of the mouse were used. As a 2-day sample, binding cells were recovered by scratching, and as 4-day and 6-day samples, suspended cells were recovered. In each culture sample, biotin-labeled cRNA was synthesized from total RNA using an Illumina TotalPrep RNA Amplification Kit (Ambion, Austin, Tex.). The biotin-labeled cRNA was mixed with Illumina MouseRef-8 Expression Beadchip (Illumina, Inc., San Diego, Calif.).

B. Quantitative RT-PCR

Total RNA was purified from the cells using TRIzol (Invitrogen). cDNA was synthesized using RevertAid™ H Minus Reverse transcriptase and Oligo dT primers (Fermentas). Quantitative PCR was performed using a SYBR green PCR Mastermix (Qiagen), RT-PCR was performed using a Maxime RT-PCR kit (iNtRON Biotechnology, Inc.). Specific sequence data of the primers used herein are shown in Table 1.

TABLE 1

| Category | Forward primer (5' → 3') | Reverse primer (5' → 3') |
|---|---|---|
| Dab2 | tgc tcg tga tgt gac aga ca (SEQ. ID. NO: 1) | agg gtc att agg gcc tca ct (SEQ. ID. NO: 2) |
| GAPDH | aat gtg tcc gtc gtg gat ct (SEQ. ID. NO: 3) | tcc acc acc ctg ttg ctg ta (SEQ. ID. NO: 4) |
| β-actin | gta tgc ctc ggt cgt acc a (SEQ. ID. NO: 5) | ctt ctg cat cct gtc agc aa (SEQ. ID. NO: 6) |

C. Western Blot Analysis

After washed with cold PBS, cells were lyzed by a lysis buffer including 50 mM Tris-HCl (pH 7.4), 150 mM NaCl, 1 mM DTIT, 30 mM NaF, 10 mM $Na_3VO_4$, 0.5% NP40, and a protease inhibitor cocktail (Pierce). Whole cell lysates were regulated using a Bradford reagent (Bio-Rad Laboratories Inc.) at the same concentration, and 40 to 120 μg of the lysate was loaded on an 8 to 12% acrylamide gel through SDS-PAGE, followed by being transferred onto a PVDF membrane (Millipore). To perform immunoblotting, the membrane was blocked with 5% non-fat dry milk prepared of TBS containing 0.5% Tween20 (TBST) at room temperature for 1 hour. In addition, the membrane was washed four times with TBST, treated with primary antibodies diluted with 4% non-fat dry milk at the optimum concentration, and cultured overnight at 4° C. After being washed with TBST four times, the membrane was cultured with HRP-binding secondary antibodies for 45 minutes. The bound antibodies were detected using a chemiluminescent HRP substrate (Millipore, USA) and an autoradiographic film (Agfa Healthcare N.V., Belgium).

D. Statistic Analysis

All of the experiments were repeated at least three times, thereby obtaining consistent results. Statistic data were expressed with a mean±SD. Comparison in means between groups was evaluated by a Student's t-test A P-value ($p<0.05$) had statistical significance.

Example 2

Knock-Down of Dab2 Gene in DC

DCs in which Dab2 is knock-down were prepared by the following method.

That is, siRNA targeting Murine Dab2 was designed and manufactured using BLOCK-IT RNAi Designer (Invitrogen) and Dharmacon RNAi Technologies (Thermo Scientific) programs. For knock-down of Dab2, two types of Dab2 siRNA were used, control siRNA was used as a control, and specific data of the respective siRNA are as follows:

```
(si-Dab2-1)
                          (SEQ. ID. NO: 7)
5'-CCU GUU GUC UAC AGU CCU U-3'

(si-Dab2-2)
                          (SEQ. ID. NO: 8)
5'-CCA CCU CUU GUU CCC UCA A-3'

(control siRNA)
                          (SEQ. ID. NO: 9)
5'-CCU UGU AUC GAC CUG UCU U-3'
```

Dab2 si-RNA (siDab2) or control siRNA (sicon) was transfected to DC precursor cells at Day 4 or Day 5 using a Lipofectamine RNAiMAX/Gene porter transfection kit (Life Technologies) and a method provided with the kit. After cultured at room temperature, 200 μl of a mixed solution was added to 2 ml of the DC culture solution. After being cultured for 4 hours, 10% FBS-contained RPMI 1640 was added at the same amount. After 24 to 48 hours, cells were washed, and used in the following experiment as Dab2 knock-down immature DC (Dab2-KD imDC).

Example 3

Detection of Dab2 Expression in Differentiation into DC

In differentiation into DCs, to detect expression of a Dab2 gene, the following experiment was performed.

First, in the differentiation into DCs, to detect the expression of the Dab2 gene at an mRNA level, expression of the Dab2 gene was detected through a microarray analysis and quantitative RT-PCR in Example 1-2 using bone marrow cells obtained from a C57BL/6 mouse. The results are shown in FIGS. 1A and 1B.

As shown in FIGS. 1A and 1B, it was confirmed that, in the differentiation of bone marrow stem cells into DCs, the expression of the Dab2 gene was increased.

Additionally, to detect the expression of the Dab2 gene during the differentiation into DCs at a protein level, expression of Dab2 proteins in bone marrow-derived DC (BM-DC) and splenic DC was detected by western blot analysis in Example 1-2. The results are shown in FIGS. 2A and 2B.

Figure 2B:
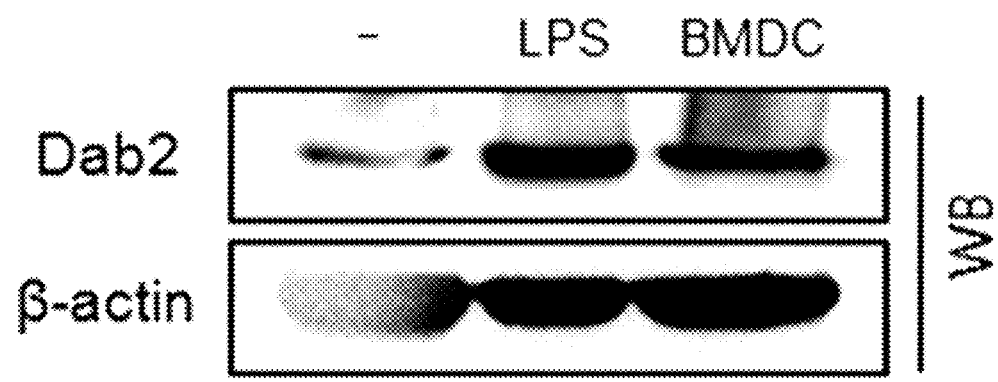

As shown in FIGS. 2A and 2B, it was confirmed that, during the differentiation of the bone marrow stem cells into DCs, the expression of a Dab2 protein was also increased.

Example 4

Detection of Changes in Phenotype and Function of DC Due to Dab2 Knock-Down 4-1. Detection of Dab2 Expression The expression of a Dab2 gene in a Dab2 knock-down DC was detected through the western blot analysis of Example 1-2, and the result is shown in FIG. 3A.

As shown in FIG. 3A, it was confirmed that, the expression of a Dab2 gene in a Dab2 knock-down DC was suppressed.

4-2. Detection of Phenotype of DC Due to Dab2 Knock-Down

To analyze a phenotype of a cell, direct immunofluorescence staining was performed. The cells were stained with the following antibodies in fluorescence-activated cell sorting (FACS) buffer at 4° C. for 20 minutes: FITC-labeled rat anti-mouse CD14 (rmC5-3), anti-mouse CD86 (GL), anti-mouse I-A/I-E (2G9), anti-mouse MHCI ($H-2K^d$), PE-labeled hamster anti-mouse CD11c (HL3), anti-mouse CD80 (16-10A1), rat anti-mouse-CD40 (3/23) (BD Pharmingen), and FITC-labeled isotype control antibodies. After the cells were washed, they were analyzed using FACS Calibur (BD) using CellQuest or FlowJo software. For intracellular Dab2 staining, the cells were prestained with a PE-labeled hamster anti-mouse CD11c antibody, followed by performing cell fixation and permiabilization using a BD Cytofix/Cytoperm™ kit (BD Bioscience Pharmingen). In addition, a rabbit anti-mouse Dab2 antibody (Proteintech) or a rabbit isotype control antibody was stained in BD Perm/wash buffer for 1 hour, and a second FITC-labeled goat anti-rabbit IgG antibody was stained. The cells were washed with BD Perm/wash buffer, and analyzed by flow cytometry. The result is shown in FIG. 3B.

As shown in FIG. 3B, it was confirmed that expression of MHCII, CD80, CD86, MHCI, and CD40, which plays a critical role in activating T cells, was increased in Dab2 knock-down DCs.

4-3. Detection of Antigen Uptake Capacity of DCs Due to Dab2 Knock-Down

Bone marrow-derived DCs (BMDCs) were produced from a C57BL/6 mouse. At day 4, Dab2 si-RNA or control si-RNA was transfected into DC precursor cells. After 48 hours, the cells were stimulated with LPS (100-200 ng/ml) for 24 hours. The cells were harvested, and $2\times10^5$ cells were stabilized in a FACS tube at 37° C. or 4° C. for 45 minutes, 1 mg/ml FITC-conjugated dextran was added, and uptaken for 1 hour. Then, the reaction was stopped with cold staining buffer. The washed cells were stained with PE-conjugated anti-CD11, and analyzed by FACS Calibur flow cytometry. The result is shown in FIG. 4.

Figure 4:
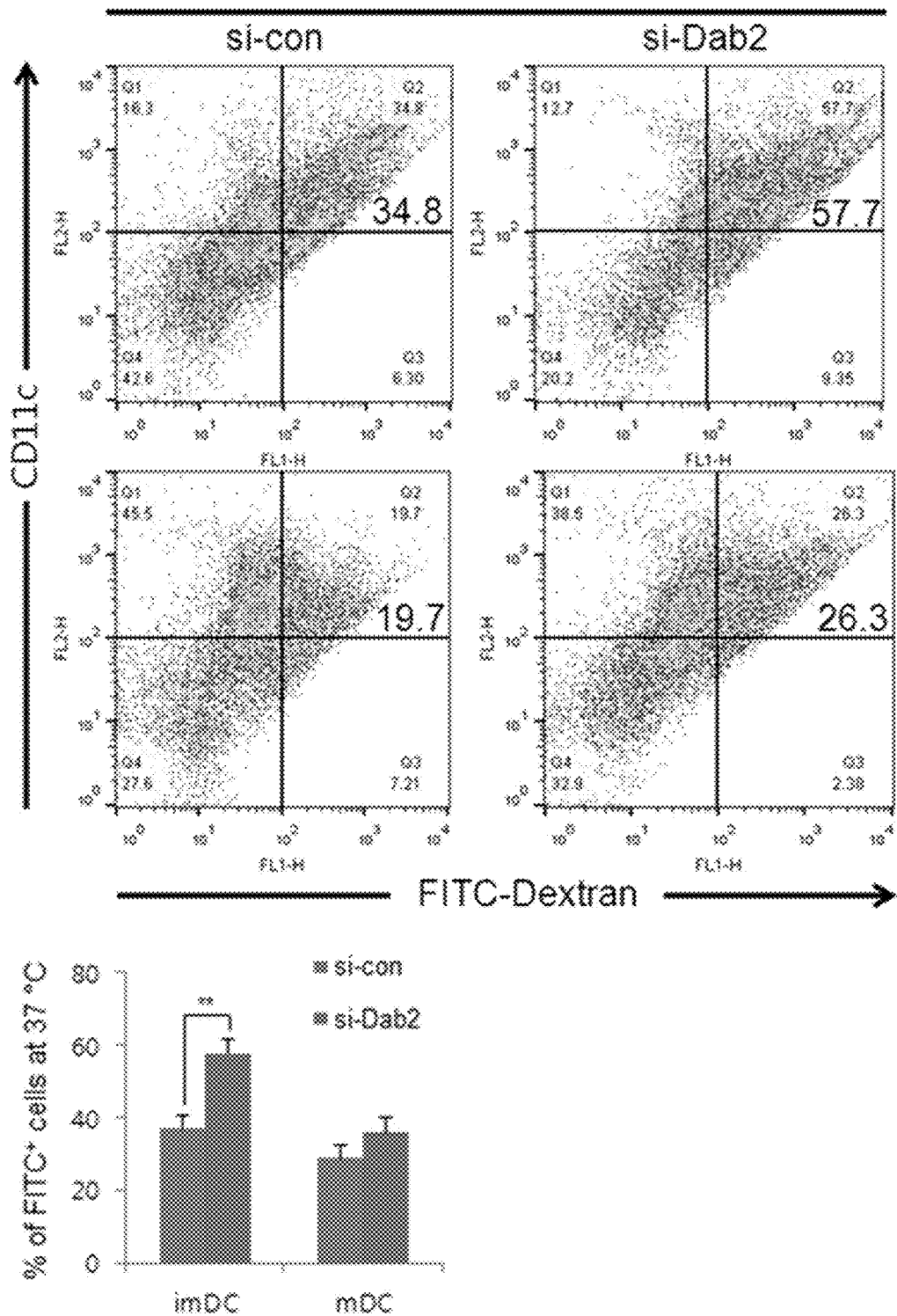
FIG. 4 shows antigen uptake capacity of DCs due to knock-down of Dab2.

As shown in FIG. 4, it was confirmed that phagocytosis in Dab2 knock-down DC was also reinforced.

4-4. Detection of Migration Capability of DCs Due to Dab2 Knock-Down

Figure 5A:
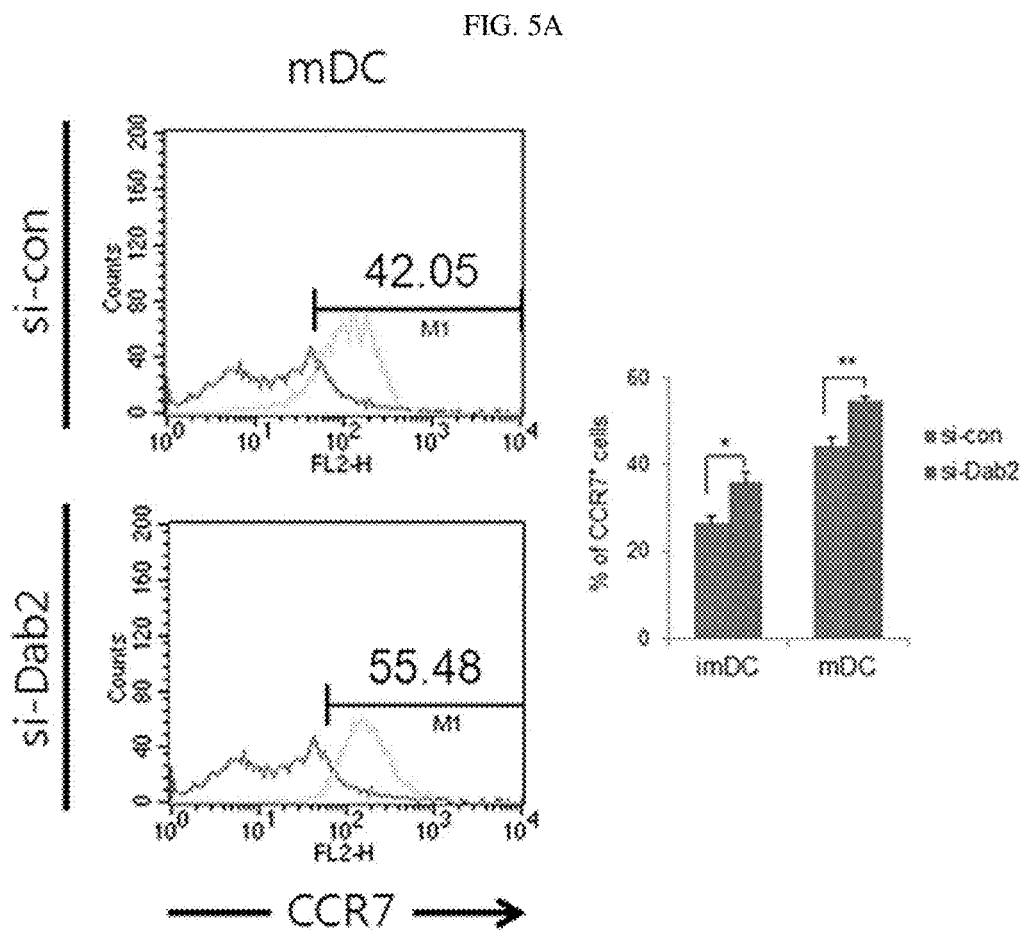
FIGS. 5A and 5B show (FIG. 5A) results of confirming whether expression of a receptor involved in cell migration, CCR7, is increased in DCs with knock-down Dab2, and (FIG. 5B) results of confirming whether there is enhancement in a migration capability of DCs to CCL19 chemokine.

First, an experiment was performed by the same method as described in Example 4-2, except that anti-mouse-CCR7 and a PE-labeled isotype control were used as antibodies, and the result is shown in FIG. 5A. As shown in FIG. 5A, it was confirmed that expression of CCR7, which is a receptor involved in cell migration, was increased in Dab2 knock-down DCs.

Subsequently, an in vitro chemotaxis assay was performed using a Transwell system. That is, chemotaxis of bone marrow-derived DCs (BMDCs) was detected by measuring a migration capability of DCs using a polycarbonate filter having an 8 µM pore size in 24-well Transwell chambers (SPL Life Sciences, Korea and Corning Costar, Cambridge, Mass.). BMDCs were differentiated from bone marrow cells of a C57BL/6 mouse. After 4 days of DC differentiation, Dab2 si-RNA or control si-RNA was transfected into DC precursor cells. After 48 hours, the cells were stimulated with LPS (100-200 ng/ml) for 24 hours, and washed with PBS. CCL19 (300 ng/ml) diluted in 0.6 ml of a serum-free RPMI 1640 medium was added in lower chambers of a Transwell plate, and mature DCs (mDCs) treated with LPS were filled in upper chambers, followed by culturing the cells in the Transwell plate in a $CO_2$ incubator at 37° C. for 3 hours. Migrated DCs were yielded from the lower chambers, and the number of DCs was measured. The results is shown in FIG. 5B.

Figure 5B:
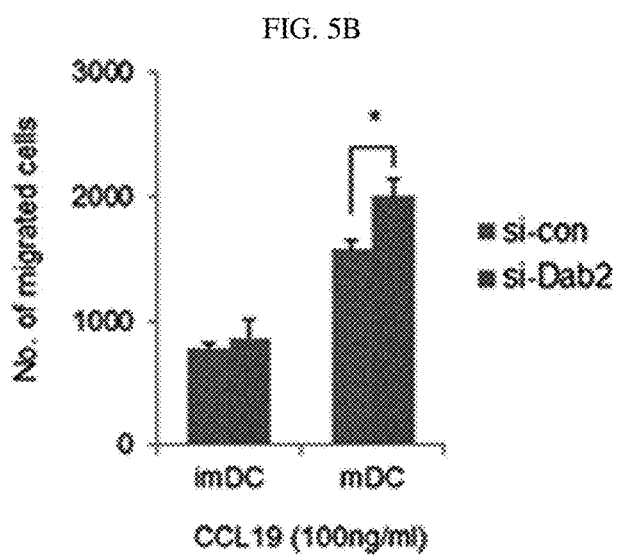

As shown in FIG. 5B, it was confirmed that chemotaxis of Dab2 knock-down DCs to CCL19 was improved.

Example 5

Detection of Change in Capability of Inducing T Cell Immunity in Dab2 Knock-Down DCs 5-1. Detection of Increase or Decrease in Secretion of Cytokines in Dab2 Knock-Down DCs An increase or decrease in expression of cytokines involved in inflammation secreted from Dab2 knock-down DCs was compared with that in control siRNA (sicon)-transfected DCs. More specifically, the cytokines secreted from bone marrow-derived DCs were detected from a supernatant of a culture solution using IL-6, IL-12p70, and a TNF-α ELISA kit, and the result is shown in FIG. 6A.

Figure 6A:
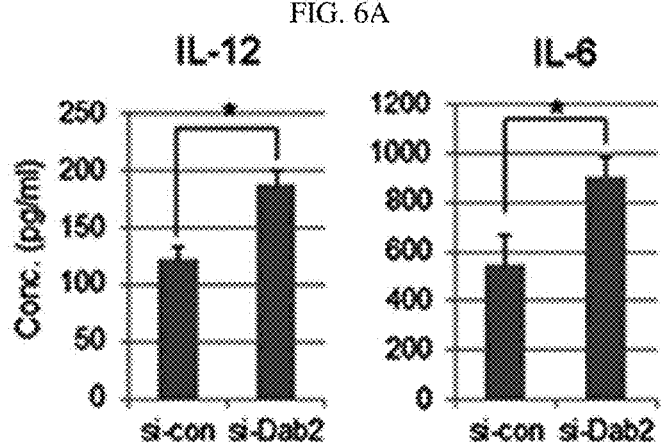

As shown in FIG. 6A, it was confirmed that, in Dab2 knock-down DCs, secretion of IL-12 and IL-6 inducing inflammation was increased with statistical significance. This means that Dab2 knock-down DCs can more effectively induce T cell proliferation and activity, and thus can increase activity of CTL suppressing occurrence or growth of cancer.

5-2. Detection of Enhanced T Cell Proliferation by DCs with Dab2 Knock-Down

Figure 6B:
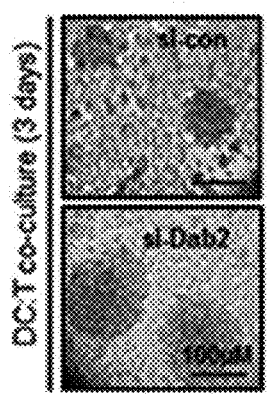

To investigate whether Dab2 knock-down DCs induces CTL activity, Dab2 knock-down DCs (DC/si-Dab2) and Dab2 normal DCs (DC/si-con) were co-cultured with OT-1 T cells, and then a colony forming assay and an MTT assay were performed to quantify T cell proliferation. Dab2 knock-down DCs and Dab2 normal DCs were treated with an $OVA_{257-264}$ (SIINFEKL; SEQ. ID. NO: 10) peptide for 1 hour, and cocultured with OT-1 T cells isolated by nylon wool columns (PolySciences Inc., Warrington, Pa., USA) from a spleen of an OT-1 mouse for 3 days in a ratio of 1:10. According to FIG. 6B, it was confirmed that T cell colonies formed by DCs were photographed with a microscope after 3 days of the coculture, and considerably larger than those formed by the Dab2 normal DCs, which was used as a control.

Figure 6C:
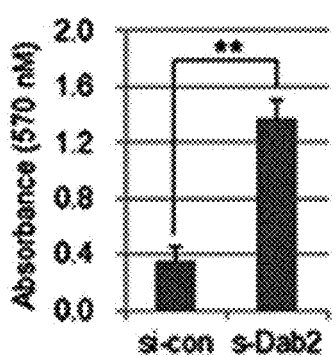

In addition, the T cells amplified as described above were quantified by a 3-(4,4-Dimethythiazol-2-yl)-2,5-diphenyltetrazolium bromide (MTT) assay. In the MTT assay, 20 µl/well of an MTT solution (5 mg/ml) was added to the cells cocultured for 3 days to induce a reaction for 4 hours, a stabilization solution was added at room temperature to stop the reaction, and an absorbance at a wavelength of 570 nm was measured. The result is shown in FIG. 6C. As shown in FIG. 6C, it was confirmed that, in Dab2 knock-down DCs, T cell proliferation was considerably greater than in Dab2 normal DCs, which was used as a control.

Moreover, to more precisely analyze proliferation of CD8 T cells directly working on anticancer activity, Dab2 knock-down DCs and Dab2 normal DCs were treated with an $OVA_{257-264}$ peptide, and cocultured for 3 days with OT-1 T cells labeled with carboxy-fluorescein diacetate succinimidyl ester (CFSE) for 1 hour, followed by analyzing the proliferated T cells by fluorescence flow cytometry. The result is shown in FIG. 6D. As shown in FIG. 6D, it was confirmed that, in Dab2 knock-down DCs, CD8 T cell proliferation was considerably greater than in Dab2 normal DCs, which was used as a control.

5-3. Detection of Increase and Decrease of Cytokines Secretion from Th Cells Co-Cultured with DCs with Dab2 Knock-Down An increase or decrease in cytokines secreted from T cells was compared when Dab2 knock-down DCs (DC/si-Dab2) or Dab2 normal DCs (DC/si-con) were cocultured with the T cells.

More specifically, Dab2 knock-down DCs (DC/si-Dab2) and Dab2 normal DCs were treated with an $OVA_{323-339}$ (ISQAVHAAHAEINEAGR; SEQ. ID. NO: 11) peptide for 1 hour, and cocultured with OT-2 T cells isolated from a spleen of an OT-2 mouse through nylon wool columns (PolySciences Inc., Warrington, Pa., USA) in a ratio of 1:10 for 3 days. After 3 days of the culture, IFN-γ, IL-17A, and IL-4 levels were measured from a supernatant using an ELISA kit (Biolegend), and the result is shown in FIG. 6E.

Figure 6E:
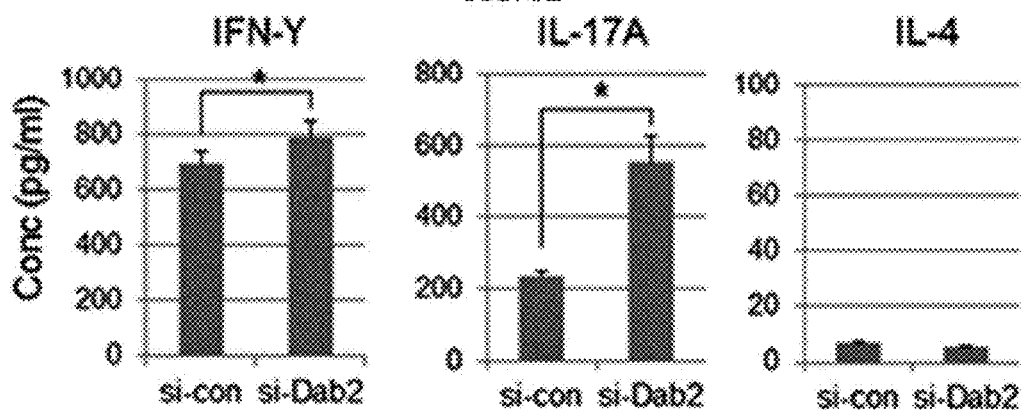

As shown in FIG. 6E, it was confirmed that IFN-γ and IL-17 secreted from the T cells proliferated by Dab2 knock-down DCs were significantly increased. However, a Th2-type cytokine, IL-4, was less secreted, and had almost no difference between the two groups. Summarizing this, it shows that Dab2 knock-down DCs could more effectively induce CD4+ T cell-mediated inflammation, for example, Th1/Th17 inflammation, and CD8+ T cell-mediated CTL activity than Dab2 normal DCs.

Figure 6F:
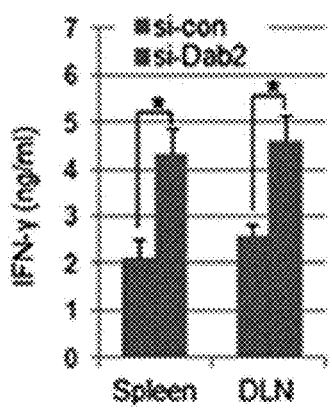

5-4. Detection of Capability of Inducing In Vivo CTL Activity of Dab2 Knock-Down DCs Dab2 knock-down DCs (DC/si-Dab2) and Dab2 normal DCs (DC/si-con) treated with an $OVA_{257-264}$ peptide (SIINFEKL; SEQ. ID. NO: 10) were injected subcutaneously into the OT-1 mouse twice at intervals of a week. After 14 days, the mouse was euthanized, and a spleen and a draining lymph node (DLN) were extracted, splenocytes and DLN cells were seeded on a 6-well plate at $2 \times 10^6$ cells/well, and cultured for a week in the presence of 10 µg/ml of an $OVA_{257-264}$ peptide (SIINFEKL; SEQ. ID. NO: 10), thereby preparing effector cells to investigate a degree of γ-interferon secretion in a supernatant of the culture solution. The result is shown in FIG. 6F. In addition, the effector cells were cultured with target cells (EL4 and E.G7) labeled with 1 μM of CFSE for 1 hour in various ratios for 4 hours. After the reaction, the cells were yielded, and stained with PI, and then CTL activity was analyzed by FACS. The result is shown in FIG. 6G.

Figure 6G:
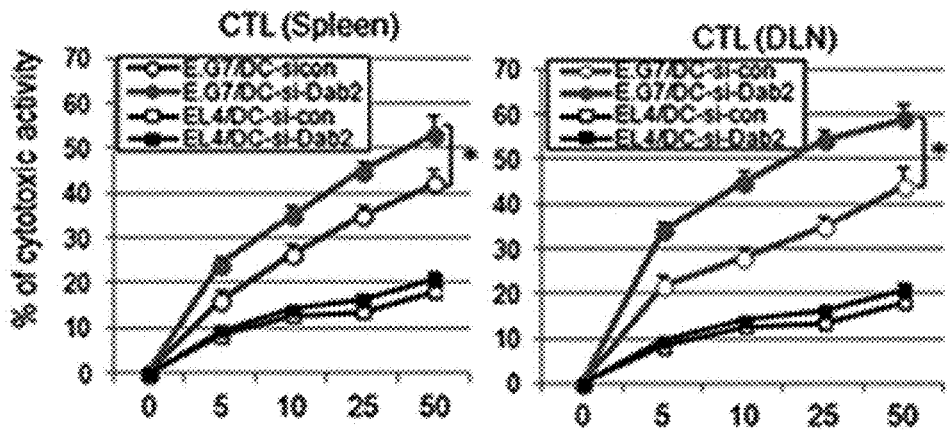

As shown in FIGS. 6F and 6G, it was confirmed that effector cells produced from the spleen and DLN of the Dab2 knock-down DC-injected mouse secreted γ-IFN much more than effector cells of the Dab2 normal DC-injected mouse did (FIG. 6F), and the CTL activity was improved (FIG. 6G). Such a result strongly suggests that anticancer immunity of Dab2 knock-down DCs can be improved.

Example 6

Detection of Anticancer Effect Using Dab2 Knock-Down DCs $5 \times 10^5$ each of EL4 and E.G7 cells were injected subcutaneously (s.c.) into a right femoral region of a C57BL/6 mouse. Dab2 knock-down DCs (DC/si-Dab2) and Dab2 normal DCs (DC/si-con) treated with an $OVA_{257-264}$ peptide (SIINFEKL) were injected into tumor-generated mice, and subcutaneously vaccinated twice at the third and tenth days after the injection of the cancer cells. Cancer growth was detected using a caliper from the seventh day at intervals of 2 to 3 days. Quantification of cancer was calculated by $V=(A^2 \times B)/2$ when a length of the shorter axis (width) is A, and a length of the longer axis is B. The result is shown in FIG. 7.

As shown in FIG. 7, as a result of performing immunotherapy using Dab2 knock-down DCs in an E.G7 tumorous mouse model expressing a chicken-derived albumin (OVA), it was confirmed that Dab2 knock-down DCs (OVA-DC/si-Dab2) treated with an OVA peptide more effectively inhibited cancer growth than Dab2 normal DCs (OVA-DC/si-con) (FIG. 7A). However, in the EL4 tumorous mouse model not expressing OVA, and an effect of suppressing the cancer growth was not shown by the above-described two DC groups (FIG. 7B). As the result, it was seen that the E.G7 tumorous mouse model showed an OVA antigen-specific anticancer effect by OVA-DC/si-Dab2.

Example 7

Figure 8A:
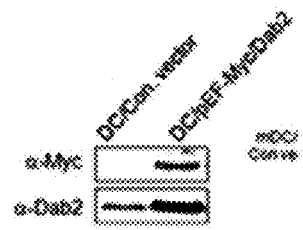

Detection of Inhibition of Anticancer Effect of Dab2 Over-Expressed DCs 7-1. Preparation of Dab2 Over-Expressed DC A Dab2 gene, p96, was amplified by PCR, cloned in a pEF-Myc plasmid vector (pEF-Myc/Dab2), transfected into bone marrow-derived DC using a Lipofectamine 2000 transfection kit after 4 days of differentiation, and then cells were harvested after 48 hours. The cells were cultured in a medium containing LPS (200 ng/ml) for 24 hours, thereby preparing Dab2-over-expressed mature DCs (mDC/pEF-Myc/Dab2). FIG. 8A shows that a Dab2 protein was over-expressed in DCs by a western blot analysis of Example 1-2 using anti-Myc and anti-Dab2 antibodies.

7-2. Detection of Phenotype of Dab2 Over-Expressed DCs

Figure 8B:
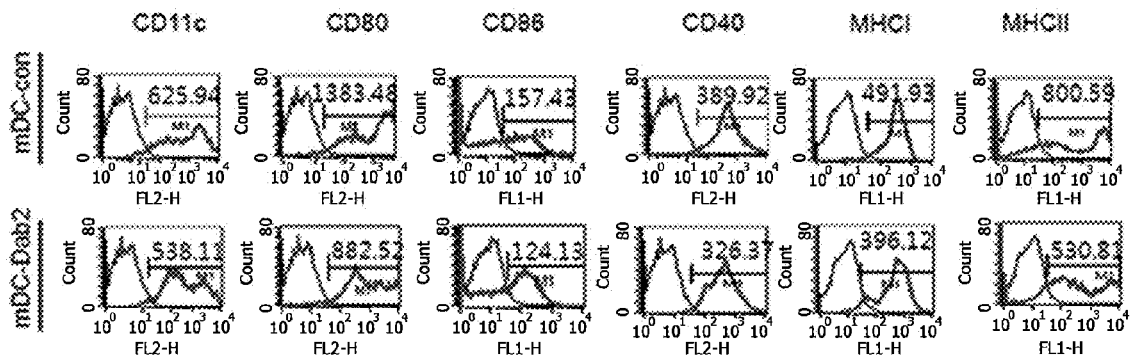

A phenotype of Dab2 over-expressed DCs was detected by the same method as described in Example 4-2, and the result is shown in FIGS. 8B and 8C.

As shown in FIGS. 8B and 8C, it was confirmed that expression of MHCI, MHCII, CD80, CD86, and CD40, important in activating T cells, was statistically significantly reduced in Dab2-over-expressed DCs, compared to a normal group (Statistic significance: *p<0.05 and **p<0.01).

7-3. Detection of Increase or Decrease in Secretion of Cytokines of Dab2-Over-Expressed DCs An increase or decrease in cytokines involved in inflammation secreted in Dab2-over-expressed DCs (mDC/pEF-Myc/Dab2) was compared with that in Dab2 normal DCs (mDC/con vector) by the same method as described in Example 5-1, and the result is shown in FIG. 8D.

As shown in FIG. 8D, it was confirmed that secretion of IL-12 involved in induction of Th1 immunity was reduced with statistical significance from Dab2 over-expressed DCs (statistical significance: *p<0.05).

7-4. Detection of Suppression of Treating Cancer in Tumorous Mouse Model

In the E.G7 tumorous mouse model expressing chicken-derived albumin (OVA) by the same method as described in Example 6, Dab over-expressed DCs treated with an $OVA_{257-264}$ peptide (SIINFEKL) (SEQ. ID. NO:10) were injected into tumor cells, and subcutaneously vaccinated twice at day 3 and 10 to observe cancer growth. The result is shown in FIG. 8E.

As shown in FIG. 8E, it was confirmed that an effect of suppressing cancer growth was considerably decreased in Dab2 over-expressed DCs treated with the OVA peptide (OVA-DC/+Dab2), compared to Dab2 normal DCs (OVA-DC/+con). It was seen that capability of inducing anticancer immunity of normal DCs was suppressed by the over-expression of Dab2.

A composition of the present disclosure includes DCs in which a Dab2 gene is knocked down or knocked out or activity of a Dab2 protein is suppressed as an active ingredient, and thus is expected to be useful as a pharmaceutical composition to prevent, improve, or treat cancer since having improved antigen uptake, a migration ability of a cell to a lymph node, and expression of inflammable cytokines, and activating antigen-specific CTL and related T cells that can attack cancer cells.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Therefore, the scope of the disclosure is defined not by the detailed description, but by the claims and their equivalents, and all variations within the scope of the claims and their equivalents are to be construed as being included in the disclosure.

What is claimed is:

1. A method of treating cancer in a subject in need thereof, comprising administering an effective amount of a pharmaceutical composition, comprising dendritic cells in which expression of a Dab2 gene or activity of a Dab2 protein is suppressed by an antisense nucleotide, siRNA, shRNA or a ribozyme, which complementarily binds to mRNA of the Dab2 gene, and in which the dendritic cells comprise an epitope of a cancer antigen, to the subject.

2. The method according to claim 1, wherein the siRNA is represented by a base sequence of SEQ. ID. NO: 7 or SEQ. ID. NO: 8.

3. The method according to claim 1, wherein, in the dendritic cells in which the expression of a Dab2 gene is suppressed, expression of MHCII, CD80, CD86 and CD40 is increased.

4. The method according to claim 1, wherein the composition increases T cell proliferation.

5. The method according to claim 4, wherein the composition increases antigen-specific cytotoxic T cell lymphocytes (CTLs).

6. A method of improving target recognition of Dab2 suppressed dendritic cells, comprising delivering an epitope to the dendritic cells, wherein expression of a Dab2 gene was suppressed by knock-down or knock-out of the Dab2 gene and the knock-down was performed by an antisense nucleotide, siRNA, shRNA or a ribozyme, which complementarily binds to mRNA of the Dab2 gene.

7. The method according to claim 6, wherein, in the dendritic cells in which the expression of a Dab2 gene is suppressed, expression of MHCII, CD80, CD86 and CD40 is increased.

8. The method according to claim 1, further comprising delivering the epitope to the dendritic cells in the pharmaceutical composition prior to administering the effective amount of the pharmaceutical composition.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Dab2 Forward primer

<400> SEQUENCE: 1
tgctcgtgat gtgacagaca                                          20

<210> SEQ ID NO 2
<211> LENGTH: 20
<212> TYPE: DNA
<213> ORGANISM: Artificial Sequence
<220> FEATURE:
<223> OTHER INFORMATION: Dab2 Reverse primer

<400> SEQUENCE: 2
agggtcatta gggcctcact                                          20

<210> SEQ ID NO 3
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 3
aatgtgtccg tcgtggatct                                          20

<210> SEQ ID NO 4
<211> LENGTH: 20
<212> TYPE: DNA
<213> ORGANISM: Artificial Sequence
<220> FEATURE:
<223> OTHER INFORMATION: GAPDH Reverse primer

<400> SEQUENCE: 4
tccaccaccc tgttgctgta                                          20

<210> SEQ ID NO 5
<211> LENGTH: 19
<212> TYPE: DNA
<213> ORGANISM: Artificial Sequence
<220> FEATURE:
<223> OTHER INFORMATION: beta-actin Forward primer

<400> SEQUENCE: 5
gtatgcctcg gtcgtacca                                           19

<210> SEQ ID NO 6
<211> LENGTH: 20
<212> TYPE: DNA
<213> ORGANISM: Artificial Sequence
<220> FEATURE:
<223> OTHER INFORMATION: beta-actin Reverse primer

<400> SEQUENCE: 6
cttctgcatc ctgtcagcaa                                          20

<210> SEQ ID NO 7
<211> LENGTH: 19
<212> TYPE: RNA
<213> ORGANISM: Artificial Sequence

```
<220> FEATURE:
<223> OTHER INFORMATION: si-Dab2-1

<400> SEQUENCE: 7
ccuguugucu acaguccuu                                                  19

<210> SEQ ID NO 8
<211> LENGTH: 19
<212> TYPE: RNA
<213> ORGANISM: Artificial Sequence
<220> FEATURE:
<223> OTHER INFORMATION: si-Dab2-2

<400> SEQUENCE: 8
ccaccucuug uucccucaa                                                  19

<210> SEQ ID NO 9
<211> LENGTH: 19
<212> TYPE: RNA
<213> ORGANISM: Artificial Sequence
<220> FEATURE:
<223> OTHER INFORMATION: control siRNA

<400> SEQUENCE: 9
ccuuguaucg accugucuu                                                  19

<210> SEQ ID NO 10
<211> LENGTH: 8
<212> TYPE: PRT
<213> ORGANISM: Artificial Sequence
<220> FEATURE:
<223> OTHER INFORMATION: OVA peptide 257-264

<400> SEQUENCE: 10

Ser Ile Ile Asn Phe Glu Lys Leu
1               5

<210> SEQ ID NO 11
<211> LENGTH: 17
<212> TYPE: PRT
<213> ORGANISM: Artificial Sequence
<220> FEATURE:
<223> OTHER INFORMATION: OVA peptide 323-339

<400> SEQUENCE: 11

Ile Ser Gln Ala Val His Ala Ala His Ala Glu Ile Asn Glu Ala Gly
1               5                   10                  15
Arg
```